United States Patent [19]
Gonzalez-Lepera

[11] Patent Number: 6,149,593
[45] Date of Patent: Nov. 21, 2000

[54] METHOD AND APPARATUS FOR DETECTING BETA RADIATION

[75] Inventor: Carlos Gonzalez-Lepera, Wallingford, Pa.

[73] Assignee: The Trustees of the University of Pennsylvania, Philadelphia, Pa.

[21] Appl. No.: 08/767,159

[22] Filed: Dec. 16, 1996

[51] Int. Cl.$^7$ .................................................. A61B 6/00
[52] U.S. Cl. .................... 600/436; 600/431; 250/303; 250/308
[58] Field of Search ................... 600/431, 436; 250/306, 307, 308, 303, 363.01, 363.03

[56] References Cited

U.S. PATENT DOCUMENTS

| | | | |
|---|---|---|---|
| 5,008,546 | 4/1991 | Mazziotta, et al. | 250/366 |
| 5,130,539 | 7/1992 | Canter | 250/306 |
| 5,432,355 | 7/1995 | Charpak | 250/583 |

OTHER PUBLICATIONS

Daghighian, et al., "Intraoperative beta probe: A device for detecting tissue labeled with positron or electron emitting isotopes during surgery," *Med Phys.*, 21(1), Jan. 1994, pp. 153–157.

C. Gonzalez–Lepera, "Positron sources produced with a medical cyclotron: advantages and some applications," *Nuclear Instruments and Methods in Physics Research B* 99(1995), pp. 824–826.

Kuhn, et al., "Intraoperative Gamma Detection Probe with Presurgical Antibody Imaging in Colon Cancer," *Arch Surg.*, vol. 126, Nov. 1991, pp. 1398–1403.

Mearini, et al., "Fabrication of an electron multiplier utilizing diamond films," *Thin Solid Films*, 253 (1994) pp. 151–156.

Mearini, et al. "Stable secondary electron emission from chemical vapor deposited diamond films coated with alkali–halides," *Appl. Phys. Lett.*, 66(2), Jan. 9, 1995, pp. 242–244.

Nieweg, et al. "Positron Emission Tomography with Flourine–18–Deoxyglucose in the Detection and Staging of Breast Cancer," *CANCER*, vol. 71, No. 12, Jun.15, 1993, pp. 3920–3925.

Raylman, et al., "Fluorine–18–Fluorodeoxyglucose–Guided Breast Cancer Surgery with a Positron–Sensitive Probe: Validation in Preclinical Studies," *Journal of Nuclear Medicine*, vol.36, No. 10, Oct. 1995, pp. 1869–1874.

Raylman, et al., "A Fiber–Optically Coupled Positron–Sensitive Surgical Probe," *Journal of Nuclear Medicine*, vol. 35, No. 5, May 1994, pp. 909–913.

Sardi, et al., "Intra–abdominal Resurrence of Colorectal Cancer Detected by Radioimmunoguided Surgery (RIGS System)," *Arch. Surg.*, vol. 124, Jan. 1989, pp. 55–59.

*Primary Examiner*—Ruth S. Smith
*Attorney, Agent, or Firm*—Woodcock Washburn Kurtz Mackiewicz & Norris LLP

[57] ABSTRACT

A method and apparatus for detecting beta particles in the presence of high gamma background using secondary electron emission (SEE) as the primary beta particle detector. Diamond-like thin films having coefficients for SEE as high as 50 are preferably used in a small hand-held probe whereby radiolabeled malignancies as small as 3 mm in diameter can be detected. An electron multiplier amplifies the secondary electron signal for generation of an audible signal or a display indicative of the level of beta radiation passing through the air-vacuum interface of the hand-held probe.

21 Claims, 2 Drawing Sheets

METHOD AND APPARATUS FOR DETECTING BETA RADIATION

FIELD OF THE INVENTION

This invention relates to a method and apparatus for detecting beta radiation.

BACKGROUND OF THE INVENTION

Interaction of ionizing radiation with matter generates, under certain conditions, the emission of electrons from the material surface. Energetic electrons or positrons impinging on a solid tend to lose energy primarily through inelastic collisions with electrons from the material. These electrons, if produced near the surface and possessing sufficient energy to surmount the surface potential barrier of the material, can escape the solid. These electrons are known as secondary electrons. Given the short escape depth usually associated with a secondary electron, secondary electron emission (SEE) is considered a "surface" effect as opposed to a "bulk" mechanism, which generally are used for detection of energetic gamma rays. Because of this, only the characteristics of the last few layers near the surface define the SEE properties for a given material.

The rate at which these phenomena occur can be described by a quantity, ($\delta$), known as the secondary-electron emission (SEE) coefficient, i.e., the number of secondary electrons that are ejected for each primary electron incident. Depending on parameters such as incident primary beta energy, the angle of particle incidence, and material composition, the average number of ejected secondary electrons per incident particle can vary from below unity, up to 5 or 6 for some oxides. For some insulators and intermetallic compounds, SEE yields may be as high as 10 to 20.

Existing beta radiation detectors, such as scintillation counters, require the presence of beta particles having sufficient energy to generate a detection event. When a beta particle passes through a suitable material, energy is absorbed, resulting in excitation of electrons in the scintillator. The energy is re-emitted as flashes of light, or scintillations, which are absorbed by the photocathode of a photo-multiplier tube. Photoelectrons are emitted, in turn, and the number of electrons emitted or to be emitted is amplified by the photo-multiplier tube. Typically, a current pulse is produced thereby. The size of the pulse is generally proportional to the number of scintillations produced, and thus to the energy lost by the particle in the scintillator.

Although devices such as scintillators can be used to detect radiation, such as beta-radiation-emitting tracers, in tumors, they have met with limited success due to their sensitivity to background gamma radiation. The range of gamma rays is large in tissue; therefore, a large accumulation of radioactivity in a distant organ can affect probe readings, leading to ambiguity in the location of the tumor. One method for avoiding the problem caused by detection of background gamma radiation is to make the detection device sensitive to only short range radiation.

Because electrons and positrons typically have short ranges in tissue, a probe sensitive only to these charged particles will usually locate radioactivity only when placed in close proximity to the sources of such activity. Although a relatively pure, high-energy beta emitter with no gamma radiation, such as phosphorus-32, can be used as a specific radioactive marker, P-32 is unsuitable for use in many applications, and most other beta-emitting isotopes have gamma emissions as well. Therefore, a detector that is also sensitive to gamma rays is likely to be affected by background gamma radiation.

The high rate of glycolysis in malignant tissue has been successfully exploited as a tumor imaging technique using Positron Emission Tomography (PET) with the glucose analogue radiopharmaceutical 2-$^{18}$F-fluoro-2-deoxy-D-glucose (FDG). Because the original PET scanners were constructed for brain imaging, PET-FDG studies typically concentrated on tumors in the central nervous system. Further developments of whole-body PET scanners extended local tumor localization with FDG to other primary sites. Widespread acceptance during the past decade of FDG as a tumor marker prompted the development of more specific intraoperative beta probes. Although beta particles show great promise for the detection of malignant tissue, the major challenge faced by existing techniques is to construct a device which is highly efficient in detecting beta particles, such as positrons, in the presence of a high annihilation gamma photon background.

One approach to detection of beta radiation, for example, in the context of surgical devices, is described in U.S. Pat. No. 5,008,546 to Mazziotta, et al. (1991), entitled "Intraoperative Beta Probe and Method of Using the Same." Mazziotta described an intraoperative radiation probe that is devised to detect radiolabelled malignant tissues by being selectively sensitive to beta radiation while insensitive to gamma radiation. However, in this device, selectivity is achieved at the price of using two scintillators to detect radiation. One of the scintillators is shielded against beta radiation, while the other is left to detect both beta and gamma radiation. The gamma radiation sensitivity of the dual probes is empirically established and used as a weighted factor to subtract the outputs of the two probes, thereby leaving a signal indicative of the beta radiation emitted by the radiolabelled tissue.

Also, Mazziotta's instrument typically requires calibration for each radio-isotope and the weighted subtraction of both signals is calculated by a computer. Such probes report a sensitivity of 4,000 cps/$\mu$Ci for point sources of $^{18}$F using a phantom 5 mm in diameter by 5 mm long with an $^{18}$F concentration of 0.5 $\mu$Ci/ml. When this source was placed in a 2.2 liter volume containing a uniform background of $^{18}$F with a concentration of 0.05 $\mu$Ci/ml and scanned, a 1 cm FWHM resolution was achieved. However, for some malignancies, metastases may occur well before the primary tumor reaches a size of 1 cm, limiting the clinical usefulness of probes of this type.

Existing beta-sensitive probes typically require extended measurement periods of approximately 10 seconds or longer over a single point to obtain statistically meaningful readings. Furthermore, because they operate by detecting differences in local radiation intensities, it often is necessary to take several measurements over the suspected area. The use of such a device in the operating room could be severely impaired, considering the difficulties of immobilizing areas of tissue for extended periods of time during surgical procedures.

What is needed, therefore, is a highly sensitive beta-radiation probe that is capable of providing information at a faster rate, typically, 1–2 mm per second or higher.

SUMMARY OF THE INVENTION

The aforementioned long-felt needs are met and problems solved by beta radiation sensors provided in accordance with the present invention. Preferably, the beta radiation sensors provide a sensing element responsive to a beta particle, the sensing element employing a preselected surface effect to produce a signal indicative of the beta particle.

In a preferred embodiment, the beta radiation sensor comprises a sensing element responsive to a beta particle, the sensing element employing a secondary electronic emission to produce a secondary electronic signal indicative of the beta particle, the sensing element being composed of a preselected material having a secondary electron emission coefficient of greater than about 10, and the sensing element being substantially insensitive to gamma radiation, and an electron multiplying device for amplifying a secondary electron signal and providing a perceptible representation of the beta particle.

Beta particle probes in accordance with the invention may further comprise a display coupled to the sensing element for receiving the signal indicative of beta radiation and producing a perceptible representation thereof.

Beta sensing probes in accordance with the present invention thus provide information at a fast rate, typically at 1 to 2 millimeters per second or higher. Such results have not heretofore been achieved in the art. The invention will be best understood by reading the following description of the embodiments in conjunction with the drawings which are first described briefly below.

DESCRIPTION OF THE EMBODIMENTS

Figure 1:
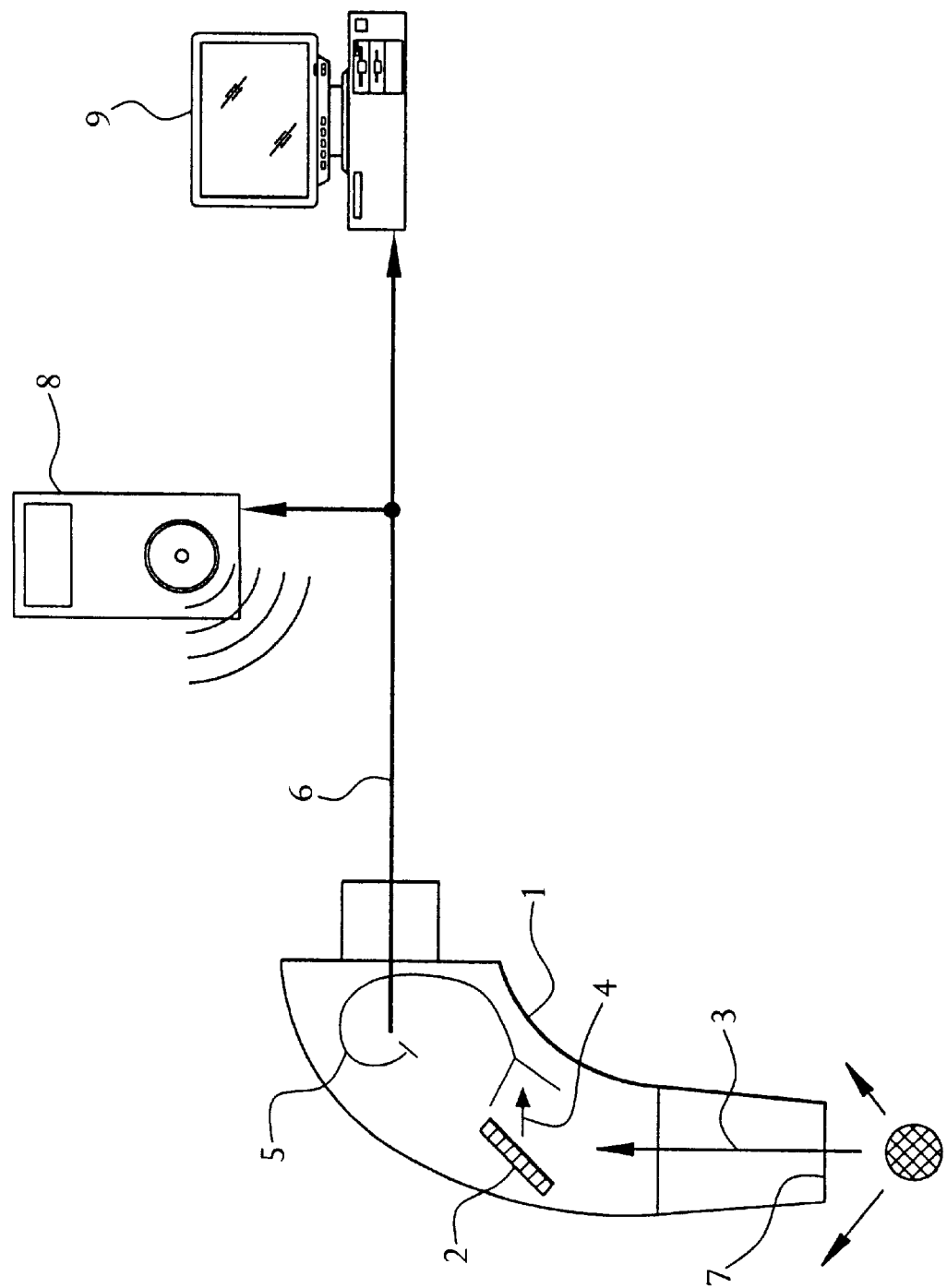
FIG. 1 is an illustration of one embodiment of the beta detector according to the invention herein.

Rapid and accurate identification of malignant tissue during surgical procedures not only assures proper removal of the affected area but also favors preservation of healthy tissue. The probability for detection and identification of breast, ovarian, stomach, pancreatic, and colorectal tumors has considerably increased since radioimmuno-guided and radiopharmaceutical-guided surgery was introduced.

There is a substantial potential to expand these techniques for cancer localization and treatment to other parts of the body as well. The main features shared by and supporting these techniques are (1) the ability of the radiolabelled agent to selectively concentrate on the malignancy; (2) the quality of the instrument employed to detect the radiolabelled agent. The embodiments of the device and method according to the present invention can significantly enhance the detection characteristics of beta-radiation probes as compared to existing devices.

In general, beta radiation is emitted according to Poisson statistics, because each decaying nucleus is independent of the others and has an equal probability of decaying per unit time. Because the uncertainty in the production of beta radiation is therefore on the order of magnitude of the square root of the number of beta rays, the more beta rays that are detected, the less the proportional uncertainty will be. Thus, sensitivity is a very important issue for the creation of images, because the rays will be detected within an area.

To get better resolution, a sufficient number of decay events, or counts, must occur so that an apparatus can resolve them spatially. Having large numbers of counts also means the apparatus must resolve them temporally. In general, attenuation and scattering inside the body mean that there will be a range of beta rays emitted, and it may be difficult to tell those scattered through very small angles from those not scattered at all. This affects the spatial resolution of the instrument. In general, energy resolution, sensitivity, and resolving time of the detector interact to produce the spatial resolution of the instrument, as well as the temporal resolution.

It is desirable to minimize the amount of ionizing radiation delivered to tissue by a source, whether the source be external to the body or, as with radionuclide-tagged materials, within the body at a tumor site. The need to minimize the radiation dose can reduce the number of counts produced, thus reducing the spatial and temporal resolution of the apparatus. This reduced resolution can lead to a reduced ability to detect and resolve malignancies. In some cases, current devices may not be able to identify nascent malignancies, allowing for aggressive tumor growth and the formation of metastases prior to detection.

A beta radiation detector according to the invention herein employs the phenomenon of secondary electron emission to detect primary beta particles incident upon the detector. Furthermore, the beta radiation detectors of the present invention are "gamma-blind", since they are primarily sensitive to beta radiation. Thin diamond-like carbon films can have a δ value ranging from 25 to as high as 50. Such high-yielding sources of secondary electrons can be employed to increase the detection probability for an incident beta particle, with subsequent increase in detector sensitivity as compared to current devices.

The secondary-electron emission mechanism can be used to provide amplification of weak electron currents using materials where the SEE coefficient exceeds unity. This well-understood mechanism has been used for many decades in photomultiplier tubes, channel electron multipliers, and more recently, multi-channel plates.

As δ becomes larger than 1, the detection probability of the primary particle is enhanced. The initial electron pulse can be further amplified many times, as is the case in discrete dynode multipliers, or continuous dynode channel electron multipliers. At the end of the amplification chain, a pulse of $10^6$ to $10^8$ electrons may be generated an easily detected with standard pulse-counting electronics.

SEE typically requires a vacuum environment as found in photomultipliers and cathode ray tubes to avoid collisions between electrons and residual gas molecules. A solid interface strong enough to support about one atmosphere of pressure differential is necessary. This interface should also be sufficiently thin to absorb only a small fraction of the beta particles or to degrade their energy within the optimum range for SEE production. Energy spectra for positrons emitted by $^{18}F$ in liquid solution traversing a 6 μm titanium foil indicate that the energy distribution of positrons emitted by the source was shifted towards lower energy levels by only few tens keV.

Typically, efficiencies for standard electron multipliers with incident electrons present a broad maximum in the energy range between one to several tens of keV. As an example of current technology, commercially-available multichannel plates have reported efficiencies close to 30% for 100 keV betas and higher than 50% at lower energies while that number drops off to about 1–2% for 500 keV gammas. Similar efficiency values based on particle stopping power considerations can be expected for incident positrons instead of electrons. Therefore, thicker and stronger foils can be used as the air-vacuum interface.

As illustrated in FIG. 1, beta radiation sensor 1 can include a sensing element 2 which is responsive to beta radiation 3 by employing a preselected nuclear surface effect, for example, secondary electron emission (SEE). In reaction to the primary incident beta radiation 3, element 2 produces a first signal 4 which is indicative of the beta radiation 3. Novelly, element 2 is used as the primary beta detection component. By contrast, when existing beta radiation sensors employ SEE components, it is not to sense primary, or incident, beta radiation 3, but typically as part of a post-sensing amplification stage.

Sensor 1 also may employ an amplifier 5 coupled with the sensing element 2 to transform first signal 4 into a second signal 6 which may more easily be detected by inexpensive components, which can provide, for example, an audio signal 8 or a visual display/computer input 9. Amplifier 5 can be an electron multiplying device such as a channel electron multiplier (channeltron), a multi-channel plate, or a photomultiplier tube.

In FIG. 1, a preferred embodiment of the present invention is presented in the form of a beta particle probe for disease detection, such as the hand-held intra-operative beta probe represented by sensor 1, although a skilled artisan would recognize that a beta radiation sensor according to the teachings herein can easily be adapted to other applications, such as, for example, non-surgical beta-detection uses, including autoradiography.

As previously noted, it is preferred to effect SEE in a vacuum to reduce attenuation of the secondary electrons by, for example, ambient gas molecules. In FIG. 1, an interface 7 can be used to create an air-vacuum barrier. Interface 7 is most preferred to be a thin foil that is substantially transparent to the passage of beta particles, for example, a 6 $\mu$m-thick titanium foil.

Figure 2:
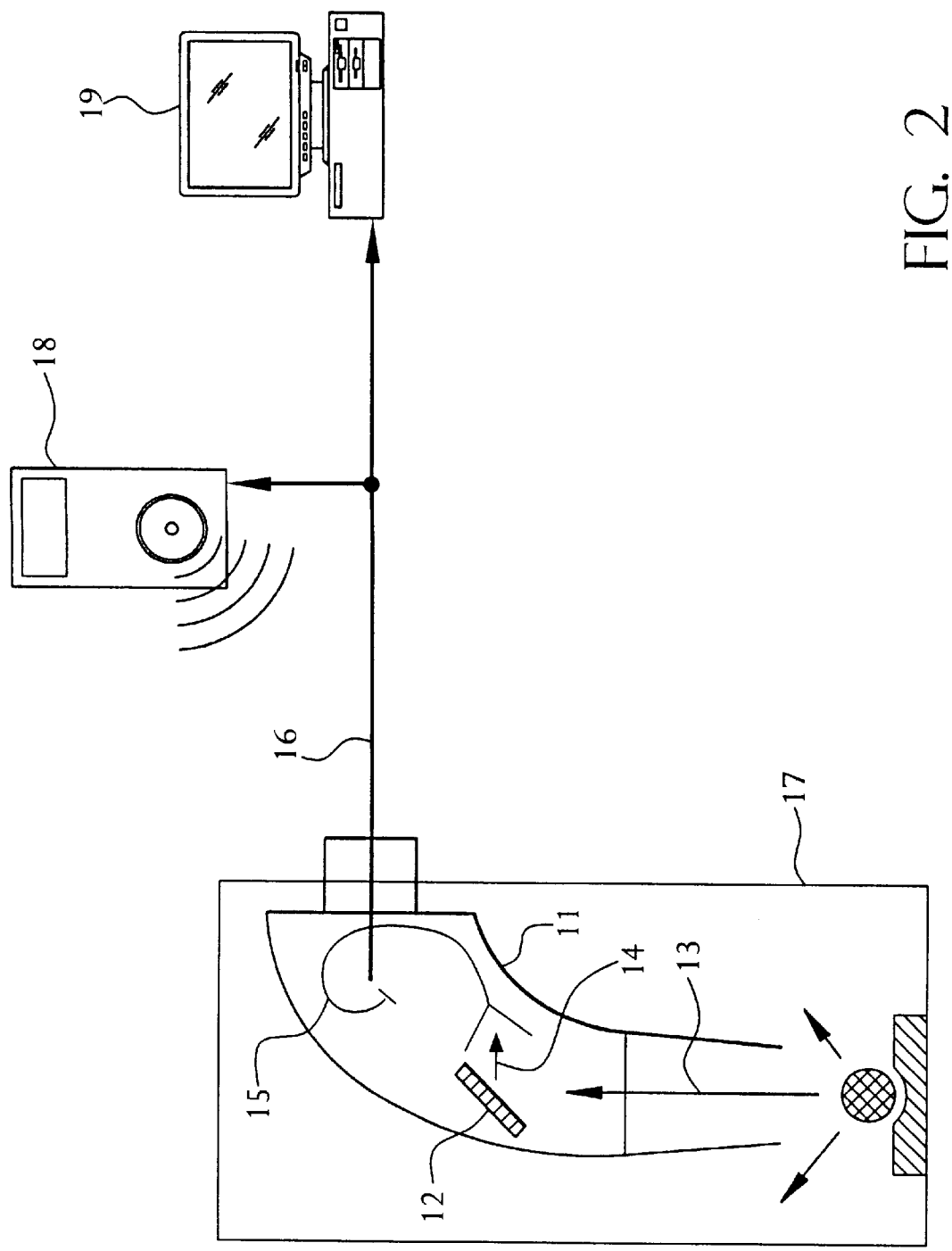
FIG. 2 is an illustration of another embodiment of the beta detector according to the invention herein.

In FIG. 2, beta radiation sensor 11 is enclosed in a chamber 17, which chamber 16 can be evacuated to reduce beta particle attenuation by, for example, ambient gas molecules. Such an arrangement can be suitable, for example, for autoradiography. Similar to FIG. 1, beta radiation sensor 11 can include a sensing element 12 which is responsive to beta radiation 13 by employing a preselected nuclear surface effect, for example, secondary electron emission (SEE). In reaction to the primary incident beta radiation 13, element 12 produces a first signal 14 which is indicative of the beta radiation 13.

Novelly, element 12 is used as the primary beta detection component. By contrast, when existing beta radiation sensors employ SEE components, it is not to sense primary, or incident, beta radiation 13, but typically as part of a post-sensing amplification stage.

Sensor 11 also may employ an amplifier 15 coupled with the sensing element 12 to transform first signal 14 into a second signal 16 which may more easily be detected by inexpensive components, for example audio/visual display 18 and video display/computer input 19. Similar to amplifier 5 in FIG. 1, amplifier 15 in FIG. 2 can be an electron multiplying device such as a channel electron multiplier (channeltron), a multi-channel plate, or a photomultiplier tube.

All publications mentioned in this specification are indicative of the level of skill of those skilled in the art to which this invention pertains. All publications are herein incorporated by reference to the same extent as if each individual publication was specifically but individually indicated to be incorporated by reference.

While specific embodiments of practicing the invention have been described in detail, it will be appreciated by those skilled in that art that various modifications and alternatives to those details could be developed in light of the overall teachings of the disclosure. Indeed, a skilled artisan would recognize that, although the invention has been described in terms of an intraoperative beta probe and an autoradiograph probe, the apparatus and method illustrated in detail herein also can be used to detect, characterize, and visualize beta particles in other milieu. Accordingly, the particular arrangements of the methods and apparatus disclosed are meant to be illustrative only and not limiting to the scope of the invention, which is to be given the full breadth of the following claims, and any and all embodiments thereof.

What is claimed is:

1. A hand-held beta radiation sensor which detects beta particles emitted by an object in the presence of background gamma particles, comprising:

a portable sealed housing enclosing a vacuum, said housing including an air-vacuum interface that is substantially transparent to the passage of beta particles and through which incident beta particles emitted by said object may pass to enter said sealed housing;

a secondary electron emission (SEE) sensor disposed in said housing so as to detect said incident beta particles which have passed through said air-vacuum interface at the substantial exclusion of said gamma particles and to generate a first signal indicative of said incident beta particles; and an amplifier which amplifies said first signal into a second signal indicative of the number of beta particles emitted by said object.

2. A beta radiation sensor as in claim 1, further comprising means responsive to said second signal for generating an audible signal representative of the number of beta particles emitted by said object.

3. A beta radiation sensor as in claim 1, further comprising means responsive to said second signal for generating a visual display representative of the number of beta particles emitted by said object.

4. A beta radiation sensor as in claim 1, wherein said air-vacuum interface comprises a thin titanium foil having a thickness of approximately 6 microns.

5. A beta radiation sensor as in claim 1, wherein said SEE sensor has an SEE coefficient of at least 10.

6. A beta radiation sensor as in claim 5, wherein said SEE sensor is a diamond-like carbon film having an SEE coefficient ranging from about 25 to about 50.

7. A beta radiation sensor as in claim 1, wherein said amplifier comprises an electron multiplier.

8. A beta radiation sensor as in claim 7, wherein said electron multiplier comprises one of a channel electron multiplier, a multi-channel plate, and a photomultiplier tube.

9. A beta radiation sensor which detects beta particles emitted by an object in the presence of background gamma particles, comprising:

a vacuum chamber adapted to contain said object and a sensor housing disposed so as to receive incident beta particles emitted by said object when said object is contained in said vacuum chamber;

a secondary electron emission (SEE) sensor disposed in said housing so as to detect said incident beta particles emitted by said object at the substantial exclusion of said gamma particles and to generate a first signal indicative of said incident beta particles; and an amplifier which amplifies said first signal into a second signal indicative of the number of beta particles emitted by said object.

10. A beta radiation sensor as in claim 9, further comprising means responsive to said second signal for generating an audible signal representative of the number of beta particles emitted by said object.

11. A beta radiation sensor as in claim 9, further comprising means responsive to said second signal for generating a visual display representative of the number of beta particles emitted by said object.

12. A beta radiation sensor as in claim 9, wherein said SEE sensor has an SEE coefficient of at least 10.

13. A beta radiation sensor as in claim 12, wherein said SEE sensor is a diamond-like carbon film having an SEE coefficient ranging from about 25 to about 50.

14. A beta radiation sensor as in claim 9, wherein said amplifier comprises an electron multiplier.

15. A beta radiation sensor as in claim 14, wherein said electron multiplier comprises one of a channel electron multiplier, a multi-channel plate, and a photomultiplier tube.

16. A method of detecting beta particles emitted by an object in the presence of background gamma particles, comprising the steps of:

disposing a sealed housing enclosing a vacuum such that incident beta particles emitted by said object may pass into said sealed housing through an air-vacuum interface of said sealed housing that is substantially transparent to the passage of said incident beta particles so as to impinge upon a secondary electron emission (SEE) sensor disposed in said housing;

said SEE sensor detecting incident beta particles which have passed through said air-vacuum interface at the substantial exclusion of said gamma particles;

generating a first signal indicative of said incident beta particles on said SEE sensor; and amplifying said first signal into a second signal indicative of the number of beta particles emitted by said object.

17. A method as in claim 16, further comprising the step of generating from said second signal an audible signal representative of the number of beta particles emitted by said object.

18. A method as in claim 16, further comprising the step of generating from said second signal a visual display representative of the number of beta particles emitted by said object.

19. A method of detecting beta particles emitted by an object in the presence of background gamma particles, comprising the steps of:

disposing said object in a vacuum chamber whereby beta particles emitted by said object may impinge upon a secondary electron emission (SEE) sensor disposed in said housing;

said SEE sensor detecting incident beta particles emitted by said object at the substantial exclusion of said gamma particles;

generating a first signal indicative of said incident beta particles on said SEE sensor; and amplifying said first signal into a second signal indicative of the number of beta particles emitted by said object.

20. A method as in claim 19, further comprising the step of generating from said second signal an audible signal representative of the number of beta particles emitted by said object.

21. A method as in claim 19, further comprising the step of generating from said second signal a visual display representative of the number of beta particles emitted by said object.

* * * * *